United States Patent
Buckley

[11] Patent Number: 6,045,520
[45] Date of Patent: Apr. 4, 2000

[54] ARTICULATED SPLINT

[75] Inventor: Stephen P. Buckley, Hingham, Mass.

[73] Assignee: Cramer Products, Inc., Gardner, Kans.

[21] Appl. No.: 09/042,522

[22] Filed: Mar. 16, 1998

[51] Int. Cl.[7] .................................................. A61F 5/00
[52] U.S. Cl. .................................................. 602/16; 602/6
[58] Field of Search .................................. 602/16, 20, 6, 602/5

[56] References Cited

U.S. PATENT DOCUMENTS

| | | |
|---|---|---|
| 2,092 | 5/1841 | Douglass . |
| 19,025 | 1/1858 | Groul . |
| 21,872 | 10/1858 | Bunce . |
| 31,501 | 2/1861 | Whitten . |
| 158,894 | 1/1875 | Bissell . |
| 161,323 | 3/1875 | Brown et al. ........................ 602/20 |
| 163,829 | 5/1875 | Westerkamp . |
| 504,218 | 8/1893 | Hoppe . |
| 552,143 | 1/1895 | Rankin . |
| 649,237 | 5/1900 | Dyson . |
| 1,089,201 | 3/1914 | Follows . |
| 1,334,596 | 3/1920 | Crouch . |
| 1,340,630 | 5/1920 | Maddox ............................... 602/20 |
| 2,339,515 | 1/1944 | Parcher . |
| 2,827,897 | 3/1958 | Pawlowki . |
| 3,745,997 | 7/1973 | Gledhill . |
| 3,943,923 | 3/1976 | Scheinberg . |
| 4,050,456 | 9/1977 | Cornue . |
| 4,169,467 | 10/1979 | Rabischong . |
| 4,209,011 | 6/1980 | Peck et al. . |
| 4,266,298 | 5/1981 | Graziano . |
| 4,270,527 | 6/1981 | Peters et al. . |
| 4,854,305 | 8/1989 | Bremer . |
| 5,000,169 | 3/1991 | Swicegood et al. . |
| 5,292,302 | 3/1994 | Gianferante . |
| 5,772,618 | 6/1998 | Mason et al. ........................ 602/16 |
| 5,797,865 | 8/1998 | McDavid, III ....................... 602/27 |
| 5,860,943 | 1/1999 | Bloedau et al. ..................... 602/16 |

*Primary Examiner*—Richard J. Apley
*Assistant Examiner*—Jayne Saydah
*Attorney, Agent, or Firm*—Litman, Kraai & Brown, L.L.C.; John C. McMahon

[57] ABSTRACT

A splint to splint injured parts of a body. The splint includes three rigid members one pair of which are joined together by a hinged joint and a second pair of which are joined by a pivot joint. The hinge joint and the pivot joint each include a locking mechanism that allows the user to select from plurality of numerous positions and thereafter lock each of the joints in a selected position. The splint is used to fix a particular body part in a selected position which may require the members to be hinged with respect to each other, pivoted with respect to each other, or both.

1 Claim, 3 Drawing Sheets

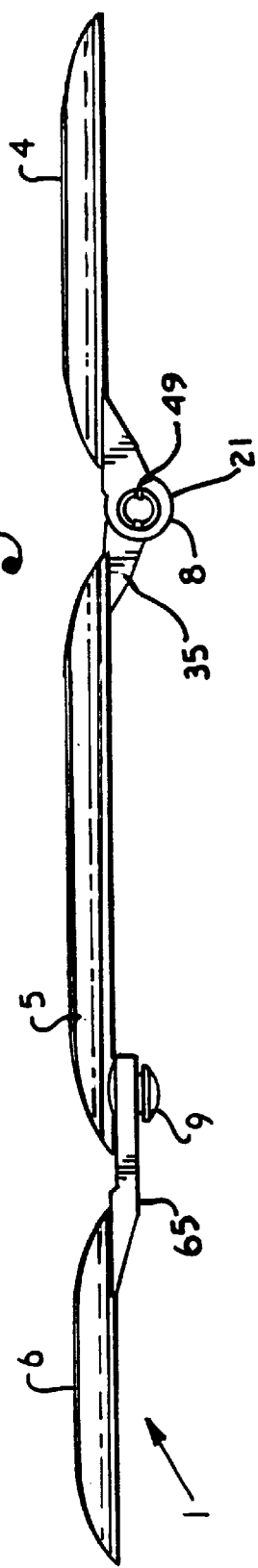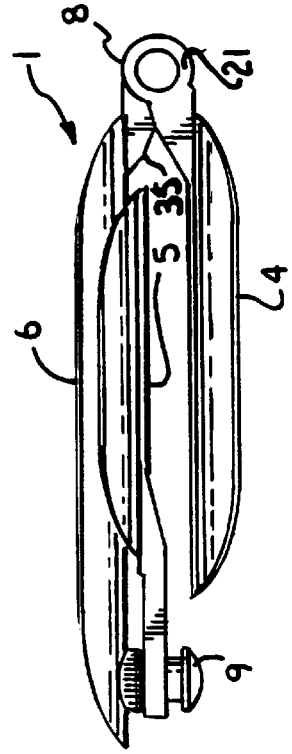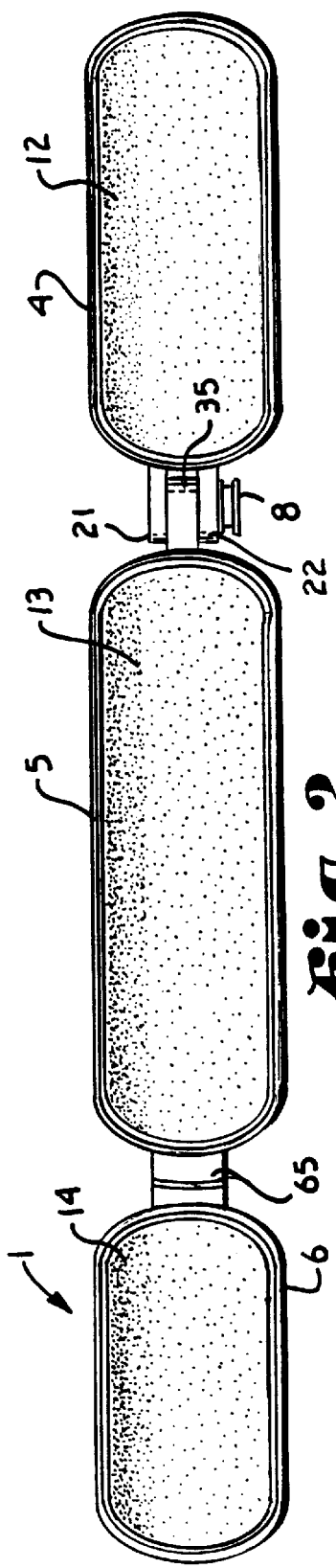

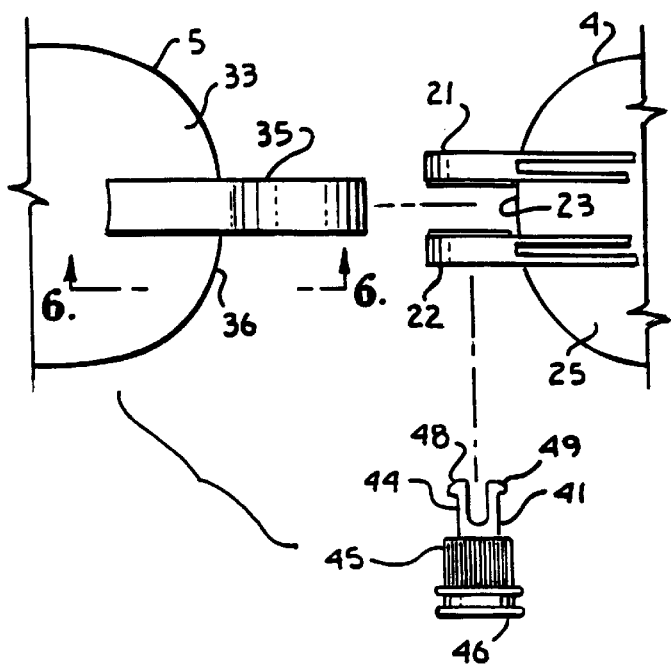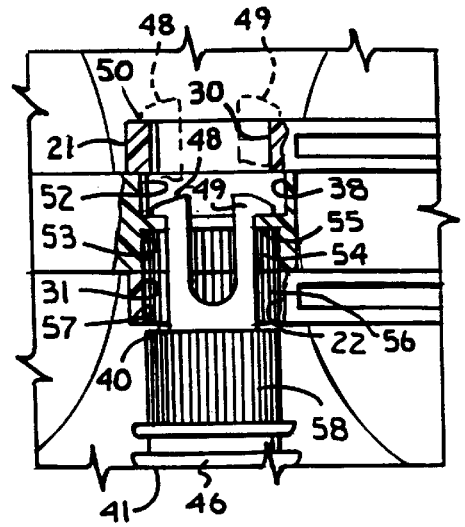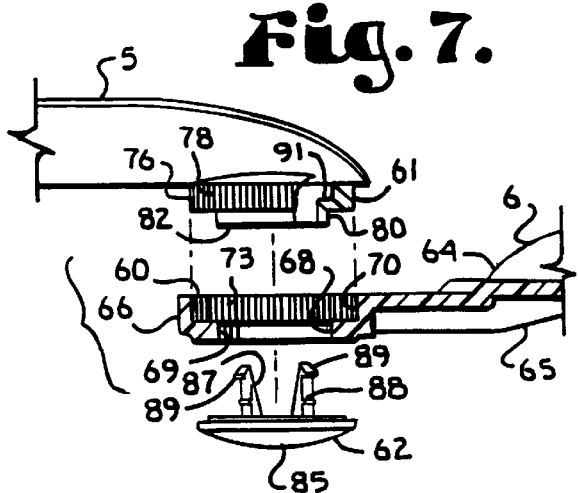

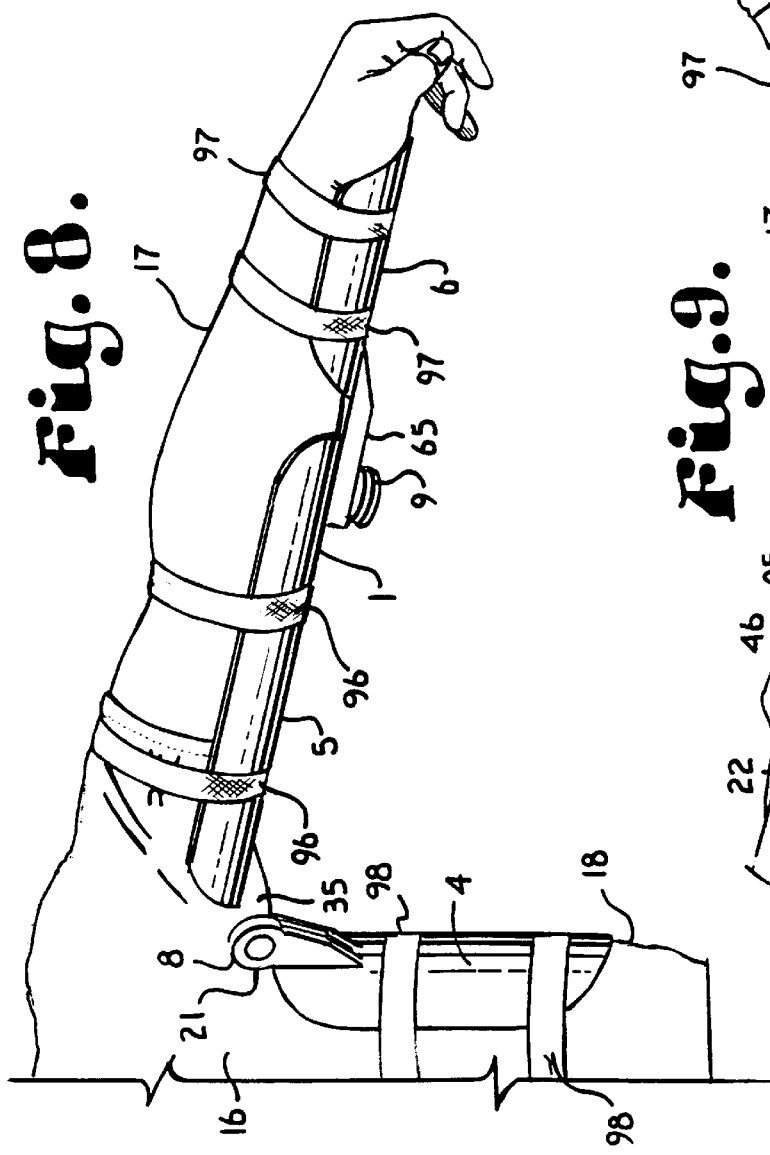
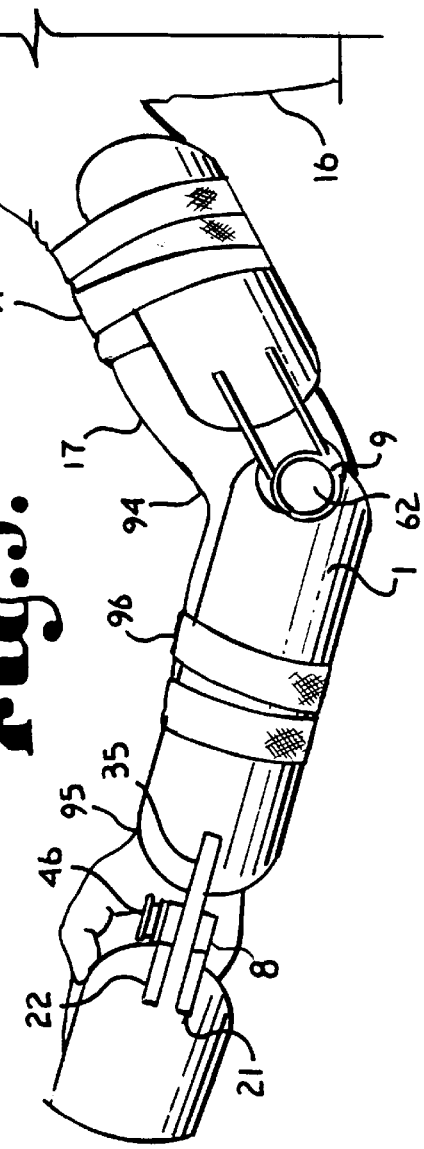

ARTICULATED SPLINT

BACKGROUND OF THE INVENTION

The present invention is directed to an articulated splint for splinting human limbs subsequent to injury and, in particular, to a splint including sections that swing with a pivotal movement or a hinge movement relative to each other in the same device and that are lockable in a plurality of selected positions relative to one another.

Sport trainers, coaches, fireman, police, emergency medical personnel persons and others who must handle limb injuries at the site of an accident or injury often need to splint a limb so that it is not bendable and/or supported during transport to a hospital or other medical facility. For example, during athletic events, arms are often dislocated, arms and legs are often broken or other injuries occur. The use of the splint varies in each of these situations. For example, with a dislocated shoulder, the splint should immobilize the arm in a comfortable position until the patient can be seen by a physician. Alternatively, an emergency medical technician may have to stabilize a leg with a compound fracture wherein a long bone is broken and then the leg is bent at the site of the break. Such a fracture requires a splint that immobilizes the leg in the broken configuration until a physician can set the leg.

In general there are many different possible uses of such a splint. In each usage, the preferred configuration of the splint is somewhat different. In some situations portions of the splint must hinge relative to each other, in some instances portions of the splint must pivot and in some instances portions of the splint must both hinge and pivot. in all situations the various portions of the splint that hinge and/or pivot should be lockable in a plurality of selected angular configurations.

It is desirable to have a single splint structure that can provide all of the above noted configurations rather than have multiple splints wherein each is designed for a specific purpose.

Most emergency workers and other persons who need to use splints also often lack a substantial amount of storage space. Consequently, it is desirable that such splints be usable in a large number of situations, yet are foldable into a compact unit and are storable in a relatively small space.

SUMMARY OF THE INVENTION

In accordance with the invention an articulating splint is provided which includes at least three elongate and substantially rigid elements that are joined together so as to be articulated with respect to each other when not in a locked configuration. Two of the elements are combined by a hinge joint whereas a second pairing of the elements is combined by a pivot joint. This allows the splint to be utilized in situations where a body member must be splinted in either a hinged or pivoted configuration or both. The hinge joint and pivot joint are each selectively lockable in a plurality of various positions which become fixed when the joint is locked.

OBJECTS AND ADVANTAGES OF THE INVENTION

Therefore, the objects of the present invention are: to provide an articulated splint having a plurality of sections wherein at least a pair of the sections are combined by a hinge joint to be used to fix and position a hinged body member and another pair of the sections are combined by a pivot joint to allow for the splint to be used to fix and position a pivoted body member, or a combination of the two; to provide such a splint wherein the hinge joint and the pivot joint are each lockable in a selected plurality of different positions; to provide such a splint which is foldable to a comparatively compact size; to provide such a splint which can be utilized in a wide variety of situations to replace individual splints which can only be used in specific situations; to provide such a splint which is comparatively easy to use, inexpensive to produce and easily storable with other emergency equipment; and to provide such a splint which is especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a side elevational view of an articulated splint in accordance with the present invention showing the splint fully unfolded and with the various members of the splint aligned along a common axis.

FIG. 2 is a top plan view of the splint in the same configuration as shown for FIG. 1.

FIG. 3 is a side elevational view of the splint with the various members folded into a storage configuration.

FIG. 4 is an enlarged, fragmentary and exploded bottom plan view of the splint, showing a hinge joint for joining two adjoining members of the splint and a lock for the hinge joint.

FIG. 5 is an enlarged, fragmentary and bottom plan view of the splint showing the lock member holding together the various portions of the hinge joint.

FIG. 6 is an enlarged and fragmentary side elevational view of a portion of the hinge joint, taken along line 6—6 of FIG. 4.

FIG. 7 is an enlarged, fragmentary, exploded and side elevational view of a pivot joint joining two members of the splint with portions broken away to show greater detail thereof.

FIG. 8 is a perspective view of the splint with a person utilizing the splint to support an injured arm.

FIG. 9 is a perspective view of the splint with a second person utilizing the splint to support the second person's arm in a different configuration from that of FIG. 8.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates an articulated splint in accordance with the present invention. The articulated splint 1 includes a first member 4, a second member 5 and a third member 6. The members 4 and 5 are joined by a hinge joint or hinge 8. Member 5 is pivotally joined to member 6 by a pivot joint or pivot 9.

Each of the members 4, 5 and 6 are elongate and shaped to engage the body parts of a user. Each of the members 4, 5 and 6 have a curved body engaging surface 12, 13 and 14 respectively. The body engaging surfaces 12, 13 and 14 are designed to cradle various body parts such as an arm 17 or a side 18 of a user 16 (see FIGS. 8 and 9).

Each of the members 4, 5 and 6 is substantially longer than it is wide. Preferably, each of the members 4, 5 and 6 are relatively thin with and, therefore, comparatively lightweight. The only major requirement for thickness is to insure that each of the members 4, 5 and 6 is sufficiently strong to satisfy the requirements of the function. The member 4, 5 and 6 are preferably constructed of a strong, resilient and at least semi-rigid or rigid plastic.

The hinge joint 8 is seen in better detail in FIGS. 4, 5 and 6. In particular, the hinge joint 8 includes first and second pin receiving supports 21 and 22 that are mounted on and extend axially outward from a distal end 23 of member 4. The supports 21 and 22 are fixedly mounted by integral molding or gluing to a rear side 25 of member 4. Located in each of the supports 21 and 22 are bores 30 and 31 respectively. The bores 30 and 31 are facing and coaxially aligned.

Mounted on an underside 33 of the member 5 by integral molding, gluing or the like is a third support 35. The third support 35 extends outwardly from the member 5 along the central axis of the member 5 from an end 36. Located in the support 35 is a pin receiving bore 38. When the supports 21 and 22 are joined and aligned with the support 35, the bores 30, 31 and 38 are coaxial so as to form a continuous opening 40. Received in the opening 40 is a hinge pin 41. The opening 40 is aligned such that a central axis thereof is perpendicular to the longitudinal axes of the members 4 and 5.

The hinge pin 41 has a first position that allows selectively rotation of the member 5 relative to the member 4 about the axis through the opening 40 so as to provide a hinge movement. As used herein, the hinge movement allows for rotation about an axis which extends from side to side of members 4 and 5 and which is substantially perpendicular to the longitudinal main axis of each of the members 4 and 5.

The pin 41 includes a bifurcated tail 44, a body 45 and a cap 46. The tail 44 has two opposed hooks 48 and 49. When the pin 41 is fully placed within the opening 40, the hooks 48 and 49 extend over the end 50 of the support 21 so as to grasp the support 21, which can be seen by the phantom lines in FIG. 5.

As can be seen in FIG. 5, the interior of bore 38 is divided into several sections. In particular, the first section 52 is smooth walled, the second section 53 has a series of axially aligned, evenly spaced and alternating grooves and peaks 54 that form serrations and that alternate circumferentially around the entire interior of the section 53. The bore 31 also has an interior 56 with a series of grooves and peaks 57 that are axially alignable with the grooves and peaks 54 when the members 4 and 5 are joined but can rotate to a plurality of different alignments when the pin 41 is in a nonlocking position thereof (solid lines in FIG. 5). The sections 52 and 53 are divided by a partial annular wall 55 that extends radially inward. The pin body 45 also has alternating grooves and peaks 58 on the outer surface thereof that mate with the grooves and peaks 54 and 57 in such a manner as to allow the body 45 to slide into and essentially lock with the section 53 on the interior of the bore 31.

In this manner, when the pin 41 is inserted such that the body 45 is entirely within the bores 31 and 38, the grooves and peaks 58 on the pin 41 abut with and lock with the opposite element of grooves and peaks 54 and 57 in the bore 31 and in bore section 53 so as to prevent any relative movement between the members 4 and 5.

When the pin is withdrawn such as is shown in FIG. 5, then the two members 4 and 5 are able to rotate relative to one another and a new angular configuration can be formed between them. When the pin 41 is pulled downwardly, as is shown in FIG. 5, the hooks 48 and 49 engage the wall 55 and prevent complete withdrawal of the pin 41. The hooks 48 and 49 on the tail 44 are biased to flare radially outwardly so as to grasp over an end 49 of the wall 50 when the pin 41 is fully inserted into the opening 40.

The annular wall 55 prevents over insertion of the pin 41 through the opening 40. Upon withdrawal of the pin 41, a user pulls outward axially on the cap 46 which causes the hooks 48 and 49 to be urged radially inward and to slip past the interference fit thereof with the end 49 of the wall 50, such that the pin 41 can be moved axially outwardly so as to allow a user to reposition the angular configuration between members 4 and 5.

The pivot joint 9 functions in a similar manner to the hinge joint 8, but is somewhat simpler in construction and allows pivotal movement rather than hinge movement. The pivot joint 9 includes a first element 60, a second element 61 and a pivot pin 62.

The first element 60 is rigidly secured to an end 64 of member 6 opposite the end 36 to which the hinge joint 8 is secured. The first element 60 has a support 65 that is attached to the member 6 by integral molding, gluing or the like on one end and has a ring 66 attached to the opposite end. The ring 66 has an internal bore 68 that has an axis that is perpendicular to both longitudinal axes of the members 5 and 6 and that extends from front to back relative to the members 5 and 6 (that is, from to top to bottom in FIG. 7).

The bore 68 has a first portion 69 of comparatively smaller radius that is smooth walled and round and a second portion 70 that is larger in diameter. The interior of the second portion 70 has a series of peaks and valleys or serrations 73 at even spacings circumferentially positioned about the interior of the second portion 70.

The second element 61 includes a ring 76 fixedly secured to the member 5. The ring 76 has an outer surface covered with circumferentially spaced peaks and valleys or serrations 78 that are sized and shaped to be received in the bore second portion 69 of the first element 60. When the peaks and valleys 78 of the second element 61 are received in the opposed peaks and valleys 73 of the first element 60, the members 5 and 6 are locked in position relative to each other and cannot pivot.

The cap 62 includes an end cover 85 that is sized larger than the bore 68 and a pair of legs 87 and 88. The cap 62 is constructed of a flexible plastic and the legs 87 and 88 include end hooks 89 that extend outwardly such that the hooks 89 bias outwardly when the legs 87 and 88 are urged radially inwardly.

The legs 87 and 88 fit snugly in the bore 80 and may be easily passed through the bore second portion 70. When the cap 62 is positioned so that the cover 85 buts against the first element 60, the legs 87 and 88 are urged outwardly such that the hooks 80 latch over an upper edge 91 of the bore 80. In this manner the two members 5 and 6 are locked in a fixed pivotal position relative to each other. The pivotal position of the members 5 and 6 may be modified by pulling axially on the cap 62 away from the first element 60 so that the legs 87 and 88 and the hooks 89 thereof are urged inwardly against the interference fit thereof with the second element 61. After the cap 62 is moved axially (downward in FIG. 7), the first and second elements 60 and 61 may slide axially relative to each other so that the sets of peaks and valleys 73 and 78 disengage to allow a new pivotal position to be selected. Thereafter, the new position is again locked by reinserting the cap 62 until the hooks 89 pass over the end 91.

Shown in FIGS. 8 and 9 are two configurations of the splint 1, as compared to many possibilities. In FIG. 8 the arm 17 is supported by the splint 1 by locking the hinge 8 in the angular position between the members 4 and 5 in the desired location. In FIG. 9 the arm is splinted in another configuration where elbow 94 is bent and the wrist 95 is partially bent. In this configuration the members 5 and 6 are locked in a pivotal position and the members 5 and 6 are locked in a slight hinged position (each relative to the members 4, 5 and 6 being in a straight line axially). FIG. 3 shows members 5 and 6 pivoted so as to overlay each other and members 4 and 5 swung about the hinge 8 so as to overlay each other for storage or transport.

Releasable straps 96, 97 and 98 secure the members 4, 5 and 6 to the adjacent body parts.

Preferably, the hinge 8 and pivot joint 9 allow for a wide range of angular configurations. In the illustrated embodiment each can be locked in almost a complete 360 degree range with only a few degrees between each selectable configuration. It is foreseen that another locking mechanism that allows selection of a number of configurations could be used in the hinge and pivot joints.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for providing support to various limb joints; said apparatus comprising:

a) first, second and third elongate substantially rigid members; each of said members having first and second opposed ends;

b) a hinge swingably joining the first end of said first member to the second end of said second member; said hinge allowing said first and second members to assume a plurality of angular configurations relative to each other about said hinge; said hinge having an axis of rotation parallel to a width of said members;

c) a hinge lock allowing selective locking of said hinge in a selected angular configuration thereof;

d) a pivot swingably joining the first end of said second member with the first end of said third member; said pivot allowing said second and third members to assume a plurality of pivotal configurations relative to each other about said pivot; said pivot having an axis of rotation aligned from front to back of said second and third members and perpendicular to said hinge axis;

e) a pivot lock allowing selective locking of said pivot in a selected pivotal configuration thereof;

f) said hinge lock and said pivot lock each comprise a pair of mating surfaces that are slideable axially relative to each other and have a series of matable serrations thereon; when said serrations are mated, said members are fixed angularly relative to each other and when said serrations are not mated, said members are swingable about said hinge and said pivot;

g) at least a first of said hinge and pivot locks includes a pin having a locking position to hold said serrations in a locked position;

h) said pin includes at least one distal hook that is biased radially outward;

i) said first hinge and pivot lock includes a ledge to receive said hook to hold said pin in a locking configuration; and j) said hook being urged inwardly by pulling on said pin to disengage said hook and allow said pin to move to a nonlocking configuration.

* * * * *